(12) United States Patent
Siejko et al.

(10) Patent No.: US 11,213,242 B2
(45) Date of Patent: Jan. 4, 2022

(54) MORPHOLOGY-BASED ATRIAL TACHYARRHYTHMIA DETECTOR

(71) Applicant: Cardiac Pacemakers, Inc., St. Paul, MN (US)

(72) Inventors: Krzysztof Z. Siejko, Maple Grove, MN (US); David L. Perschbacher, Coon Rapids, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 175 days.

(21) Appl. No.: 16/562,590

(22) Filed: Sep. 6, 2019

(65) Prior Publication Data

US 2020/0077914 A1 Mar. 12, 2020

Related U.S. Application Data

(60) Provisional application No. 62/728,228, filed on Sep. 7, 2018.

(51) Int. Cl.
*A61B 5/00* (2006.01)
*A61B 5/363* (2021.01)
*A61B 5/352* (2021.01)

(52) U.S. Cl.
CPC .............. *A61B 5/363* (2021.01); *A61B 5/352* (2021.01)

(58) Field of Classification Search
CPC ......... A61B 5/363; A61B 5/352; A61B 5/686; A61B 5/7246; A61B 5/346–366; A61N 1/3624; A61N 1/395; A61N 1/3956
See application file for complete search history.

(56) References Cited

U.S. PATENT DOCUMENTS

| | | | | |
|---|---|---|---|---|
| 2002/0183637 A1* | 12/2002 | Kim | ......................... | A61B 5/35 600/510 |
| 2009/0192394 A1* | 7/2009 | Guttag | ............... | A61B 5/02405 600/509 |
| 2016/0023013 A1* | 1/2016 | Greenhut | ................. | A61N 1/37 600/483 |

* cited by examiner

*Primary Examiner* — Scott M. Getzow
(74) *Attorney, Agent, or Firm* — Schwegman Lundberg & Woessner, P.A.

(57) ABSTRACT

Systems and methods for detecting atrial tachyarrhythmia are discussed. An exemplary atrial tachyarrhythmia detection system includes an arrhythmia detector circuit configured to receive physiologic information of a patient, generate a morphological similarity metric between the received physiologic information and a sinus rhythm (SR) template representing a morphology of conducted sinus beats during normal SR, and generate a morphological variability metric indicative of a variability in morphology between heart beats in the received physiologic information. The arrhythmia detector circuit may detect an atrial tachyarrhythmia episode the morphological similarity and morphological variability metrics.

20 Claims, 6 Drawing Sheets

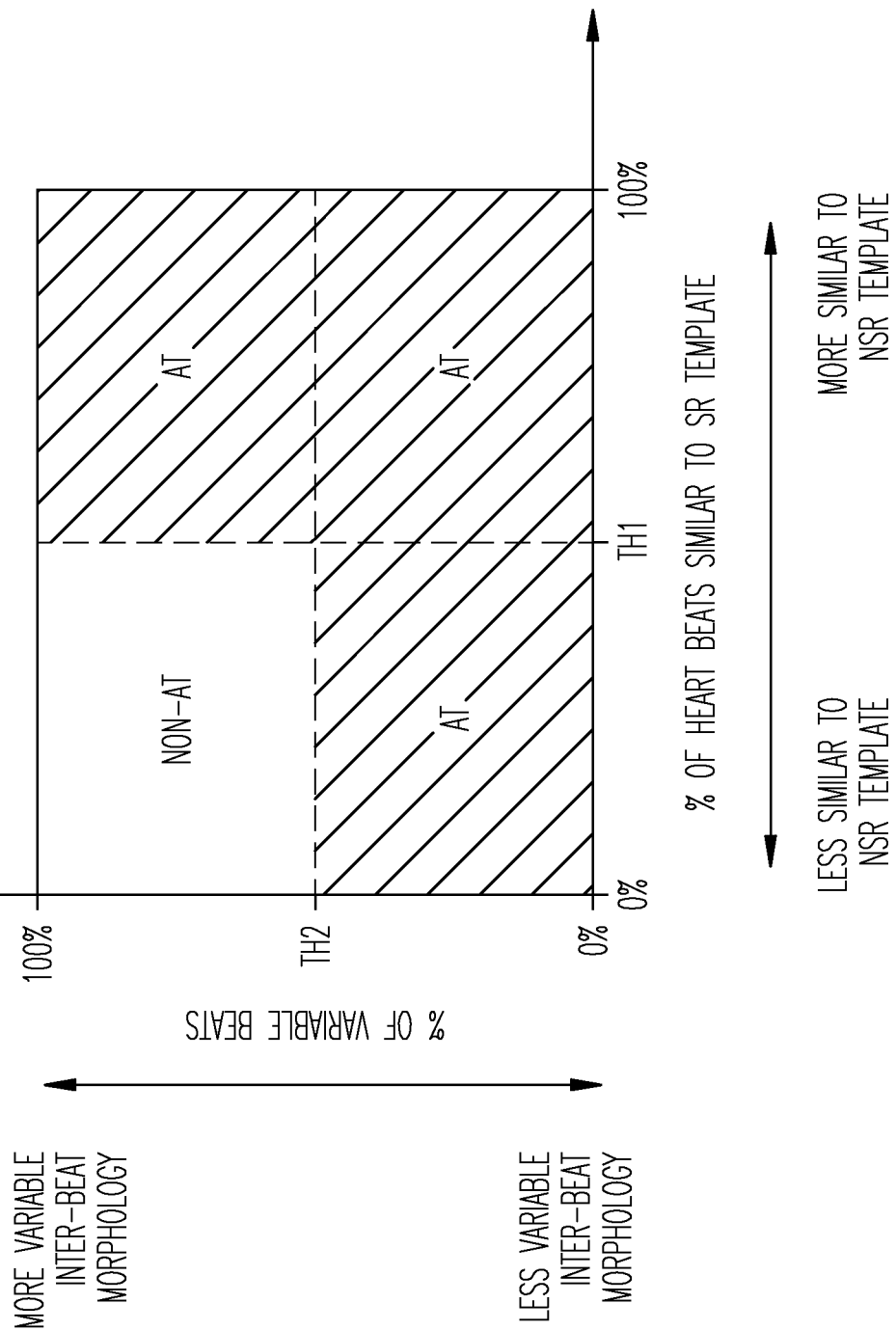

MORPHOLOGY-BASED ATRIAL TACHYARRHYTHMIA DETECTOR

CLAIM OF PRIORITY

This application claims the benefit of priority under 35 U.S.C. § 119(e) of U.S. Provisional Patent Application Ser. No. 62/728,228, filed on Sep. 7, 2018, which is herein incorporated by reference in its entirety.

TECHNICAL FIELD

This document relates generally to medical devices, and more particularly, to systems, devices and methods for detecting cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs are capable of detecting cardiac arrhythmias, such as atrial tachyarrhythmia. One type of atrial tachyarrhythmia is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself, persistent that may last for over a week and typically requires medication or other treatment to revert to normal sinus rhythm, or permanent where a normal heart rhythm cannot be restored with treatment.

Another type of atrial tachyarrhythmia is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen. Timely detection of atrial tachyarrhythmia, such as AF or AFL, may be clinically important for assessing cardiac function.

OVERVIEW

Some IMDs are capable of detecting physiologic events, such as cardiac arrhythmias or progression of chronic heart diseases, and obtaining sampled values of cardiac electrical activity signals such as electrograms. Some IMDs may further be communicated with multiple physiologic sensors that may measure various physiologic signals. Capturing accurate electrogram or other physiologic sensor information obtained over a longer period of time, such as chronically between regularly-scheduled outpatient office visits, may help the physician re-program the device, if needed, diagnose cardiac disease, or assess the patient's health status.

Atrial tachyarrhythmia such as AF or AFL are characterized by fast atrial rate. In some patients, direct sensing of atrial activation rate with an electrode positioned in the atrium is not available or not feasible, such as patients not indicated for atrial lead implantation. A medical device, such as a single-chamber IMD with no dedicated atrial sensing/pacing lead, may detect the atrial tachyarrhythmia based on heart rate, and not on direct sensing of atrial activity from the atrium. However, confounding factors such as noise, motion artifacts, or cardiac rhythms other than the atrial tachyarrhythmia may be mistakenly detected as atrial tachyarrhythmia. These false positive detections may reduce atrial tachyarrhythmia detection specificity.

Atrioventricular conduction abnormality, such as aberrant ventricular conduction, is commonly seen in patients with AF due to rapid and irregular ventricular rhythms. Aberrant ventricular conduction refers to conduction of an atrial, or supraventricular impulse to the ventricles in a markedly different manner from the usual atrioventricular impulse conduction. Aberrant ventricular conduction may be related to a sudden change in cardiac cycle length, causing refractory right or left bundle branch. The refractoriness does not allow the atrial or supraventricular impulse to propagate in that branch. Aberration is typically seen as bundle-branch-block pattern of wide QRS complex morphology, and can be mis-recognized by the medical device as ventricular arrhythmia, thereby causing false negative atrial tachyarrhythmia detections and a lower atrial tachyarrhythmia detection sensitivity.

Inappropriate atrial tachyarrhythmia detection, either false positives or false negatives, may adversely affect the device efficacy and unwarrantedly increase the healthcare cost associated with patient management. For example, false alerts to clinicians of the inappropriately detected atrial tachyarrhythmia, or presenting to clinicians a large volume of inappropriately detected arrhythmic events for review or adjudication, may diminish the clinical utility of the heart rate-based atrial tachyarrhythmia detection. Aberrant ventricular conductions that are falsely detected as ventricular tachycardia may lead to inappropriate therapies such as defibrillation shocks. For at least these reasons, the present inventors have recognized, among other things, substantial challenges and a demand for a more efficient system and methods for atrial tachyarrhythmia detection.

This document discusses, among other things, systems, devices, and methods for detecting atrial tachyarrhythmia. An atrial tachyarrhythmia detection system may include an arrhythmia detector circuit that can receive physiologic information of a patient, generate a morphological similarity metric between the received physiologic information and a sinus rhythm (SR) template representing a morphology of conducted sinus beats during normal SR, and generate a morphological variability metric representing a degree of variability between heart beats detected from the received physiologic information. The arrhythmia detector circuit may detect an atrial tachyarrhythmia episode using the morphological similarity and morphological variability metrics.

Example 1 is a system for detecting atrial tachyarrhythmia that comprises an arrhythmia detector circuit configured to: receive physiologic information of a patient; generate a morphological similarity metric between the received physiologic information and a sinus rhythm (SR) template representing a morphology of conducted sinus beats during normal SR; generate a morphological variability metric indicative of a variability in morphology between heart hearts in the received physiologic information; and detect an atrial tachyarrhythmia episode using the generated morphological similarity and morphological variability metrics.

In Example 2, the subject matter of Example 1 optionally includes the SR template that may include SR morphology features representing amplitudes of data samples of the conducted sinus beat during normal SR, and the arrhythmia detector circuit that may be configured to: detect a heart beat from the received physiologic information; generate signal features from the detected heart beat, the generated signal features including amplitudes of data samples of the detect heart beat; and compute the morphological similarity metric using the generated signal features of the detected heart beat and the SR morphology features.

In Example 3, the subject matter of Example 2 optionally includes the arrhythmia detector circuit that may be configured to align the detected heart beat with the conducted sinus beat corresponding to the SR template using a fiducial point of the detected heart beat and a fiducial point of the conducted sinus beat corresponding to the SR template.

In Example 4, the subject matter of any one or more of Examples 2-3 optionally includes the arrhythmia detector circuit that may be configured to generate the morphological similarity metric using an accumulated difference between the generated signal features of the detected heart beat and the SR morphology features.

In Example 5, the subject matter of any one or more of Examples 2-3 optionally includes the arrhythmia detector circuit that may be configured to generate the morphological similarity metric using an accumulated difference between (1) the generated signal features of the detected heart beat each weighted by a peak amplitude of the detected heart beat and (2) the SR morphology features each weighted by a peak amplitude of the conducted sinus beat.

In Example 6, the subject matter of any one or more of Examples 2-3 optionally includes the arrhythmia detector circuit that may be configured to generate the morphological similarity metric using a correlation between the generated signal features of the detected heart beat and the SR morphology features.

In Example 7, the subject matter of any one or more of Examples 1-6 optionally includes a template circuit configured to generate or update the SR template using a physiologic signal sensed during the SR.

In Example 8, the subject matter of Example 7 optionally includes the template circuit that may be configured to generate or update the SR template including to compute an ensemble average of a plurality of conducted sinus beats during normal SR, and to generate the SR morphology features from the computed ensemble average of the conducted sinus beats during the SR.

In Example 9, the subject matter of any one or more of Examples 1-8 optionally includes the arrhythmia detector circuit that may be configured to: detect first and second heart beats from the received physiologic information; align the first heart beat with the second heart beat with respect to respective fiducial points of the first and second heart beats; generate first and second signal features respectively from the aligned first and second heart beats; and compute the morphological variability metric indicative of a dissimilarity between the generated first and second signal features.

In Example 10, the subject matter of Example 9 optionally includes the generated first and second signal features that may include amplitudes of data samples taken respectively from the aligned first and second heart beats.

In Example 11, the subject matter of any one or more of Examples 9-10 optionally includes the arrhythmia detector circuit that may be configured to compute the morphological variability metric using an accumulated difference between the generated first and second signal features.

In Example 12, the subject matter of any one or more of Examples 9-10 optionally includes the arrhythmia detector circuit that may be configured to compute the morphological variability metric using an accumulated difference between (1) the generated first signal features each weighted by a peak amplitude of the detected first heart beat and (2) the generated second signal features each weighted by a peak amplitude of the detected second heart beat.

In Example 13, the subject matter of any one or more of Examples 1-12 optionally includes the arrhythmia detector circuit that may be configured to: determine a first count of heart beats, from the received physiologic information 1, with corresponding morphology similarity metric exceeding a morphology similarity threshold; determine a second count of heart beats, from the received physiologic information, with corresponding morphological variability metric exceeding a morphological variability threshold; and detect an atrial tachyarrhythmia episode using the first and second counts of heart beats.

In Example 14, the subject matter of Example 13 optionally includes the arrhythmia detector circuit that may be configured to detect an atrial tachyarrhythmia episode in response to the first count of heart beats exceeding a first count threshold, or the second count of heart beats falling below a second count threshold.

In Example 15, the subject matter of any one or more of Examples 1-14 optionally includes a therapy circuit configured to initiate or adjust a therapy in response to the detected atrial tachyarrhythmia episode.

Example 16 is a method for detecting atrial tachyarrhythmia that comprises steps of: receiving physiologic information of a patient; generating a morphological similarity metric between the received physiologic information and a sinus rhythm (SR) template representing a morphology of conducted sinus beats during normal SR; generating a morphological variability metric indicative of a variability in morphology between heart hearts in the received physiologic information; and detecting an atrial tachyarrhythmia episode using the generated morphological similarity and morphological variability metrics.

In Example 17, the subject matter of Example 16 optionally includes the SR template that may include SR morphology features representing amplitudes of data samples of the conducted sinus beat during normal SR. The method comprises steps of detecting a heart beat from the received physiologic information; generating signal features from the detected heart beat, the generated signal features including amplitudes of data samples of the detect heart beat, and computing the morphological similarity metric using the generated signal features of the detected heart beat and the SR morphology features.

In Example 18, the subject matter of Example 17 optionally includes generating the morphological similarity metric includes using an accumulated difference between (1) the generated signal features of the detected heart beat each weighted by a peak amplitude of the detected heart beat and (2) the SR morphology features each weighted by a peak amplitude of the conducted sinus beat corresponding to the SR template.

In Example 19, the subject matter of any one or more of Examples 16-18 optionally includes generating or updating the SR template using an ensemble average of conducted sinus beats detected from a physiologic signal sensed during the SR.

In Example 20, the subject matter of any one or more of Examples 16-19 optionally includes generating the morphological variability metric that may include steps of: detecting first and second heart beats from the received physiologic information; aligning the first heart beat with the second heart beat with respect to respective fiducial points of the first and second heart beats; generating first and second signal features respectively from the aligned first and second heart beats; and computing the morphological variability metric indicative of a dissimilarity between the generated first and second signal features.

In Example 21, the subject matter of Example 20 optionally includes computing the morphological variability metric using an accumulated difference between (1) the generated first signal features each weighted by a peak amplitude of the detected first heart beat and (2) the generated second signal features each weighted by a peak amplitude of the detected second heart beat.

In Example 22, the subject matter of any one or more of Examples 16-21 optionally includes detecting the atrial tachyarrhythmia episode that may include: from the received physiologic information, determining a first count of heart beats with corresponding morphology similarity metric exceeding a morphology similarity threshold, and a second count of heart beats with corresponding morphological variability metric exceeding a morphological variability threshold; and detect an atrial tachyarrhythmia episode if the first count of heart beats exceeding a first count threshold, or if he second count of heart beats falling below a second count threshold.

In Example 23, the subject matter of any one or more of Examples 16-22 optionally includes comprising initiating or adjusting a therapy in response to the detected atrial tachyarrhythmia episode.

The systems, devices, and methods discussed in this document may improve the medical technology of automated cardiac rhythm management and prevention of worsening of cardiac function. Atrial arrhythmia detection based on morphological similarity to a sinus rhythm template, and a morphological variability between heart beats in a physiologic signal, enhance the performance and functionality of an ambulatory cardiac device. For example, although aberrant ventricular conduction during atrial fibrillation may present with wide QRS morphology different from a normal sinus rhythm morphology, the conducted beats nevertheless may have little beat-to-beat variability in morphology, such that the morphological variability metric discussed herein may help recognize atrial fibrillation episodes and increase sensitivity of existing atrial arrhythmia detection. Therefore, system performance can be improved with little to no additional cost, while reducing costs associated with false AF or AFL detection, or manual inspection required by such false determinations. In other examples, existing system performance can be maintained (e.g., high AF or AFL sensitivity and specificity, etc.) using lower cost or less obtrusive systems, apparatus, and methods. For example, because the system or device does not require direct atrial activity sensing for atrial tachyarrhythmia detection, the system complexity and implementation cost may be reduced. It may particularly be beneficial for patient not indicated for atrial lead implantation either for atrial activity sensing or for atrial pacing. Moreover, the atrial tachyarrhythmia detection discussed herein may help improve the efficiency device memory usage. Both the morphological similarity metric and the morphological variability metric are clinically relevant to arrhythmia recognition. As fewer alarms are provided, battery life can be extended, fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 4 is a graph illustrating an exemplary scheme of detecting atrial tachyarrhythmia using the morphological similarity metric and the morphological variability metric.

DETAILED DESCRIPTION

Disclosed herein are systems, devices, and methods for detecting atrial tachyarrhythmia. An atrial tachyarrhythmia detection system may include an arrhythmia detector circuit configured to receive physiologic information of a patient, generate a morphological similarity metric between the received physiologic information and a sinus rhythm template representing a morphology of conducted sinus beats during normal sinus rhythm, and a morphological variability metric indicative of a variability in morphology between heart beats in the received physiologic information. The arrhythmia detector circuit may detect an atrial tachyarrhythmia episode using the morphological similarity and morphological variability metrics.

Figure 1:
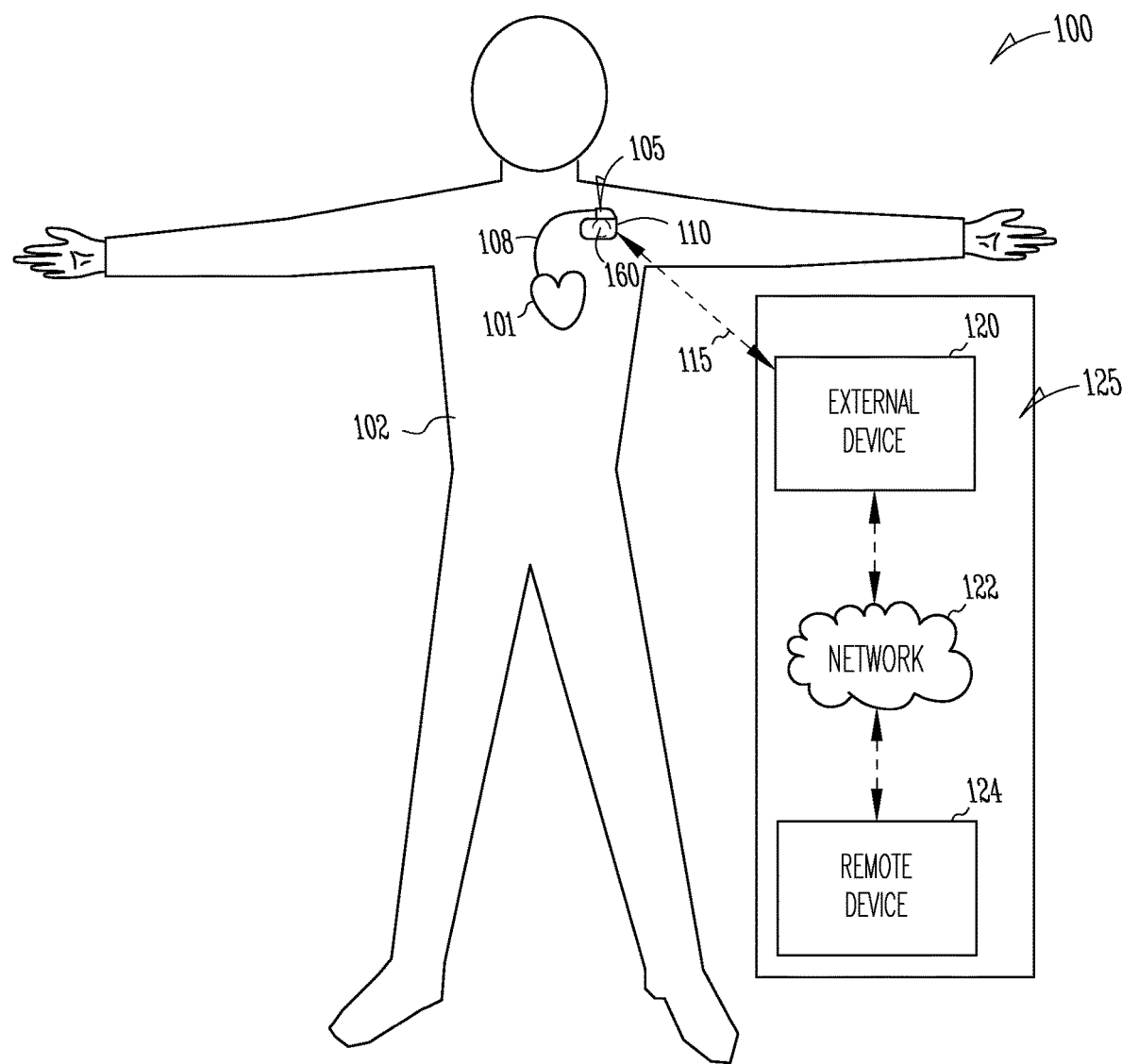
FIG. 1 illustrates an example of a Cardiac Rhythm Management (CRM) system and portions of an environment in which the CRM system may operate.

FIG. 1 illustrates generally an example of a patient management system and portions of an environment in which the system 100 may operate. The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices, wearable medical devices, or other external monitoring or therapeutic medical devices or equipment.

The AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be configured to be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

In an example, the AMD 110 may include a cardiac arrhythmia detection circuit 160 configured to detect an atrial tachyarrhythmia from the patient 102. The cardiac arrhythmia detection circuit 160 may sense a physiologic signal, such as an electrocardiograph (ECG) or an intracardiac electrogram (EGM). The cardiac arrhythmia detection circuit 160 may detect heart beats using the physiologic signal, generate a morphological similarity metric between the received physiologic signal and a SR template representing a morphology of conducted sinus beats during normal SR, and generate a morphological variability metric indicative of variability between the heart beats in the received physiologic signal. The cardiac arrhythmia detection circuit 160 may detect atrial tachyarrhythmia, such as an atrial fibrillation (AF) episode or an atrial flutter (AFL) episode, using the morphological similarity and morphological variability metrics. The AMD 110 may output the detected atrial tachyarrhythmia to a user such as the patient or a clinician, or to a process including, for example, an instance of a computer program executable in a microprocessor. In an example, the process may include an automated generation of recommendations for anti-arrhythmic therapy, or a recommendation for further diagnostic test or treatment.

The AMD 110 may include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmias, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmias or complications from arrhythmias.

Although the discussion herein with respect to the AMD 110 focuses on implantable system, this is meant only by way of example and not limitation. It is within the contemplation of the inventors and within the scope of this document, that the systems, devices, and methods discussed herein may also be implemented in, and executed by, a subcutaneous medical device such as a subcutaneous monitor or diagnostic device, wearable medical devices (e.g., watch-like devices, patch-based devices, or other accessories), or other ambulatory medical devices.

The external system 125 may be communicated with the AMD 110 via a communication link 115. The external system 125 may include a dedicated hardware/software system such as a programmer, a remote server-based patient management system, or alternatively a system defined predominantly by software running on a standard personal computer. The external system 125 may be used to control the operation of the AMD 110. The external system 125 may additionally receive via the communication link 115 information acquired by AMD 110, such as one or more physiologic signals.

By way of example and not limitation, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiologic data acquired by the AMD 110, extracting physiologic data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiologic data, performing at least one self-diagnostic test (such as for a device operational status), analyzing the physiologic data to detect cardiac arrhythmias, or optionally delivering or adjusting a therapy to the patient 102.

One or more of the external device 120 or the remote device 124 may include a display for displaying the physiologic or functional signals, or alerts, alarms, emergency calls, or other forms of warnings to signal the detection of arrhythmias. In some examples, the external system 125 may include an external data processor configured to analyze the physiologic or functional signals received by the AMD 110, and to confirm or reject the detection of arrhythmias. Computationally intensive algorithms, such as machine-learning algorithms, may be implemented in the external data processor to process the data retrospectively to detect cardia arrhythmias.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
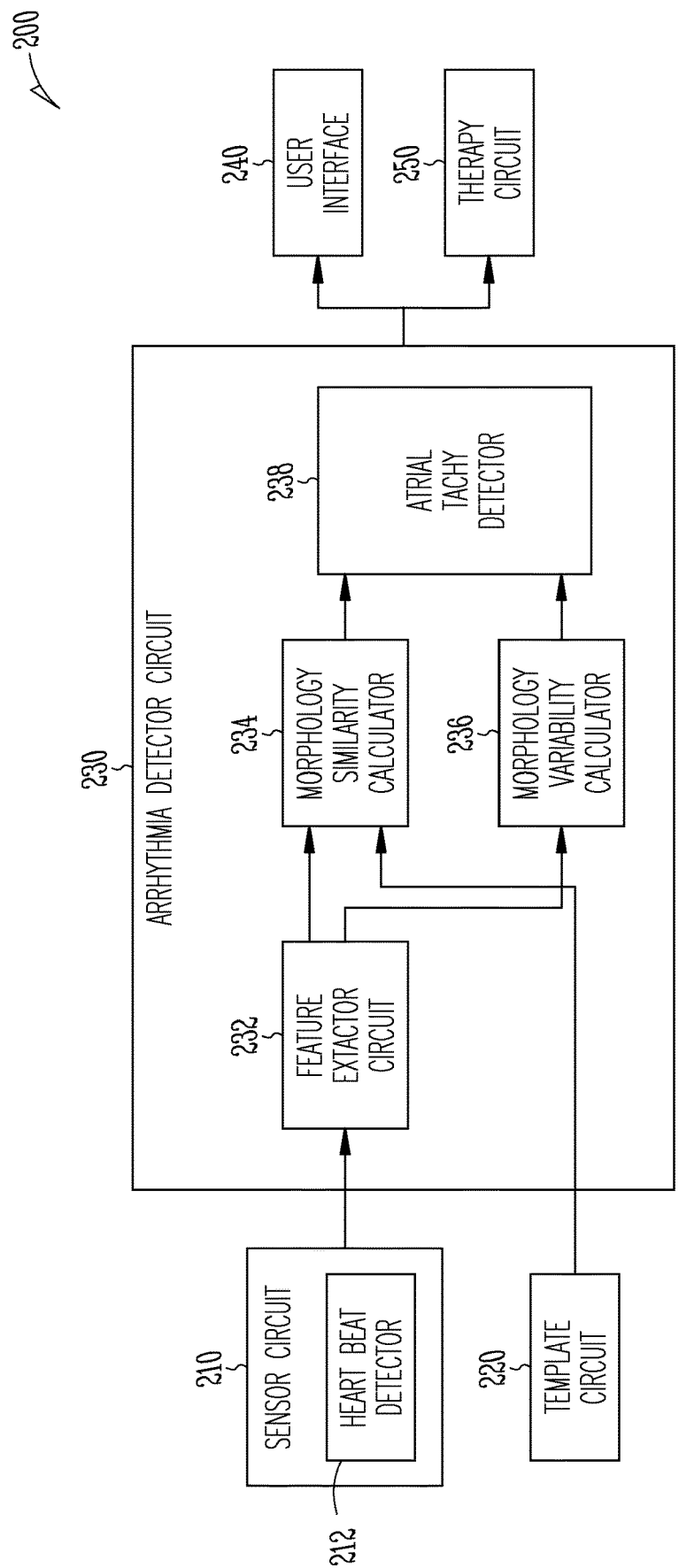
FIG. 2 illustrates generally an example of an arrhythmia detection system configured to detect cardiac arrhythmia in a patient.

FIG. 2 illustrates generally an example of an arrhythmia detection system 200 configured to detect cardiac arrhythmia in a patient, such as an atrial tachyarrhythmia episode. Portions of the arrhythmia detection 200 may be included in the arrhythmia detection circuit 160 of the AMD 110. The arrhythmia detection system 200 may include one or more of a sensor circuit 210, a template circuit 220, an arrhythmia detector circuit 230, a user interface 240, and a therapy circuit 250.

The sensor circuit 210 may include a sense amplifier circuit to sense a physiologic signal sensed from a patient via one or more implantable, wearable, or otherwise ambulatory sensors or electrodes associated with the patient. The sensed physiologic signal may contain information about pulsatile cardiac activity, such as heart rate or pulse rate. Examples of the physiologic signals may include surface ECG such as sensed from electrodes on the body surface, subcutaneous ECG such as sensed from electrodes placed under the skin, intracardiac EGM sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiologic signal.

In some examples, patient physiologic information may be stored in a storage device, such as an electronic medical record (EMR) system. The sensor circuit 210 may be configured to retrieve patient physiologic information from the storage device in response to a command signal that is provided by a system user, or automatically generated in response to occurrence of a specific event.

The sensor circuit 210 includes a heart beat detector 212 configured to detect heart beats from the sensed physiologic signal or the received patient physiologic information. In an example, the physiologic signal or information may include a cardiac electrical signal, such as an ECG, a subcutaneous ECG, or an intracardiac EGM, and the heart beat detector 212 may detect electrophysiologic events indicative of cardiac depolarization or repolarization. Examples of the sensed electrophysiologic events may include P wave, Q wave, R wave, QRS complex, or T wave in a surface or subcutaneous ECG or an intracardiac EGM. Additionally or alternatively, the sensor circuit 210 may be coupled to one or more sensors configured to sense cardiac mechanical activity, and the heart beat detector 212 may sense mechano-physiologic events indicative of one or more of atrial contraction, ventricular contraction, end of filling, end of emptying, or other specified phase during a cardiac contraction cycle. Examples of the sensors for sensing cardiac mechanical activity may include an accelerometer or a microphone configured to sense a heart sound signal or an endocardial acceleration signal from the heart, an impedance sensor configured to sense cyclic changes in cardiac impedance as a result of cardiac contractions, or a blood pressure sensor or a blood flow sensor for sensing pulsatile arterial pressure or flow as a result of cyclic cardiac contractions and opening/closure of heart valves, among other sensors. Examples of the mechano-physiologic events may include: S1, S2, S3, or S4 heart sound from the sensed heart sound signal, peak or trough impedance from the cardiac impedance signal, or peak or trough blood pressure from the blood pressure signal, among others.

The template circuit 220 may receive a sinus rhythm (SR) template representing a morphology of conducted sinus beats during normal sinus rhythm. A conducted sinus beat originates from the sinus node, and conducted via the physiologic atrioventricular conduction pathway to the ventricle, causing ventricular depolarization and mechanical contraction. The SR template may include SR morphology features extracted from a cardiac electrical signal (e.g. an ECG or a ventricular EGM) sensed during normal SR. The SR morphology features may include amplitudes of data samples of the cardiac electrical signal X(t) within a cardiac cycle, or a portion of the cardiac cycle such as a segment around the QRS complex. In some examples, a subset of data samples in a cardiac cycle may be selected to form the SR template. By way of example and not limitation, the SR morphology features may include a peak amplitude of a QRS complex (or of a ventricular EGM peak), and amplitudes of a number data samples on the left and/or right of the QRS or EGM peak of the conducted sinus beat. The resultant SR template {X(i)} includes N SR morphology features, {X(1), X(2), . . . , X(N)}. The SR morphology features may be arranged according to their timing in the cardiac electrical signal. In some examples, the SR template may additionally include timing information of each signal feature, such as time offsets with respect to a fiducial point (e.g., a QRS peak). In some examples, an SR template may include statistical features derived from the data samples of the conducted sinus beat. Examples of the statistical features may include local maxima and minima, signal amplitude at inflection points, maximum positive slope, maximum negative slope, etc. Examples of the SR template, and comparison of the SR template to heart beats detected from a subject, are discussed below with reference to FIGS. 3A-3C.

The template circuit 220 may receive the SR template from a storage device included in, or separate from, the arrhythmia detection system 200. Alternatively, the template circuit 220 may automatically generate a SR template, or update an existing SR template, for example, using information from the patient. In an example, the template circuit 220 may compute an ensemble average of a plurality of conducted sinus beats, and extract SR morphology features from the ensemble average to form a SR template. In some examples, the conducted sinus beats may be screened against some specific constraints, and only those sinus beats that meet said constraints are used to form the SR template. Examples of the constraints may include one or more of consistent polarity, relatively low and stable heart rate, and consistent morphology similar to a candidate template formed using an iterative signal averaging method. These constraints help to ensure that the static template will represent the patient's nominal baseline QRS morphology. The template circuit 220 may update the SR template periodically at scheduled time period (e.g., every 1-5 hours, or every day), or in response to user command or a triggering event. The SR template update allows capture of slowly evolving changes in the morphology of the baseline QRS complex.

The arrhythmia detector circuit 230 is coupled to the sensor circuit 210 and the template circuit 220, and configured to detect atrial tachyarrhythmia from the received physiologic signal. Examples of atrial tachyarrhythmia may include atrial fibrillation (AF), atrial flutter (AFL), atrial tachycardia, or paroxysmal supraventricular tachycardia (PSVT), among others. In an example, the arrhythmia detector circuit 230 may be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the arrhythmia detector circuit 230 may include circuit sets comprising a feature extractor circuit 232, a morphology similarity calculator 234, a morphology variability calculator 236, and an atrial tachyarrhythmia detector 238. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The feature extractor circuit 232 is configured to extract morphological features from the physiologic signal for physiologic information over a time period, such as from a heart beat detected from the received physiologic signal over a time period. The morphological features {Y(i)} of the sensed physiologic signal may include amplitude of data samples of the sensed physiologic signal Y(t) within a cardiac cycle or a portion of the cardiac cycle such as the QRS complex. In an example, the morphological features {Y(i)} may include amplitudes of a subset of the data samples that are selected in a manner similar to the SR morphology features in a SR template. For example, the morphological features {Y(i)} may include the QRS or EGM peak of the detected heart beat, and a specified number of data samples neighboring the QRS or EGM peak of the detected heart beat within a cardiac cycle. In an example, the detected heart beat may be aligned to the conducted sinus beat corresponding to the SR template before extracting the morphological features {Y(i)} from the detected heart beat. The alignment may be with respect to a fiducial point on the detected heart beat and a fiducial point on the conducted sinus beat corresponding to the SR template. In an example, the fiducial points include a peak of the detected heart beat, and a peak of the conducted sinus beat. Such a beat alignment may help facilitate morphological features extraction from the detected heart beat from Y(t), especially when the morphological features are extracted at specific time offset with respect to a fiducial point. In an example, the resultant signal morphological features {Y(1), Y(2), . . . , Y(N)} for the detected beat has the same number (N) of features as the SR template {X(1), X(2), . . . , X(N)}.

The morphology similarity calculator 234 may compute a morphological similarity metric $S_{XY}$ between a heart beat "k" detected from the sensed physiological signal Y(t) over a specific time period and the SR template. In an example, the morphological similarity metric may be computed using a correlation between the morphological features {Y(i)} of the detected heart beat "k" and the SR template {X(i)}. In another example, the morphological similarity metric may be computed using an accumulated difference between {Y(i)} and {X(i)}, that is, $$S_{XY}(k)=\Sigma_{i=1}^{N}|Y(i)-X(i)| \qquad (1)$$

In another example, to account for difference in signal amplitudes between the SR template and detected heart beat "k", the signal features {Y(i)} and the SR morphology features {X(i)} may be normalized before calculating the accumulated difference. In an example, the features of the SR template{X(i)} may be weighted by a peak amplitude $R_X$ of the SR template, and the detected of the heart beat "k" {Y(i)} may be weighted by a peak amplitude $R_Y$ of the detected heart beat "k". The morphological similarity metric $S_{XY}$ may be computed using accumulated weighted difference:

$$S_{XY}(k) = \sum_{i=1}^{N} |R_Y \cdot Y(i) - R_X \cdot X(i)| \quad (2)$$

When the QRS or EGM peak is one of the SR template features {X(i)}, the weight factor $R_X$=max {X(i)} for i=1, 2, ..., N. Similarly, when the QRS or EGM peak is one of the signal features {Y(i)} of the heart beat "k", the weight factor $R_Y$=max {Y(i)} for i=1, 2, ..., N.

In an example, the morphological similarity metric $S_{XY}$ may be normalized by the weighted accumulated feature amplitudes of the detected heart beat, that is, $$S_{XY}(k) = 1 - \sum_{i=1}^{N} |R_Y \cdot Y(i) - R_X \cdot X(i)| / \sum_{i=1}^{N} |R_Y \cdot Y(i)| \quad (3)$$

The resultant normalized morphological similarity metric $S_{XY}$ is a bounded value between 0 and 1, which represents a degree of similarity between {X(i)} and {Y(i)}. A smaller value (closer to "0") indicates the detected heart beat (e.g., beat "k") of the sensed physiologic signal Y(t) is morphologically distinct from the SR template, and a larger value (close to "1") indicates morphologically similar to the SR template.

The morphology variability calculator 236 is configured to generate a morphological variability metric of the sensed physiologic signal Y(t) over the time period. The morphological variability metric may be represented by beat-to-beat variability between heart beats detected from the sensed physiologic signal. In an example, the morphology variability calculator 236 may align first and second heart beats using timings of respective fiducial points, such as their respective QRS or EGM peaks. In an example, the first and second heart beats may be consecutive heart beats in the received physiologic signal.

First signal features {$Y_1$(i)} may be extracted from the aligned first heart beat, and second signal features {$Y_2$(i)} may be extracted from the aligned second heart beat. The first and second signal features may have the same number of signal features. The {$Y_1$(i)} and {$Y_2$(i)} may be generated respectively using similar feature extraction method to that described above for determining SR morphology features. In an examples, the {$Y_1$(i)} and {$Y_2$(i)} may each include amplitudes of a subset of the data samples selected from the first and second heart beats, respectively. In an example, the {$Y_1$(i)} and {$Y_2$(i)} have the same number (e.g., N) of morphology features as the SR template {X(i)}. In another example, the {$Y_1$(i)} and {$Y_2$(i)} may include features selected using a different method from the SR morphology feature formation. For example, the SR template {X(i)} has N features, and both {$Y_1$(i)} and {$Y_2$(i)} have M (M≠N) features.

The morphology variability calculator 236 may generate a morphological variability metric $V_Y$ between the heart beats detected from the sensed physiologic signal Y(t) over a specific time period. In an example, the time period of the physiologic signal Y(t) for generating the morphological variability metric $V_Y$ may be the same as the time period of the physiologic signal Y(t) for generating the morphological similarity metric $S_{XY}$. In another example, the time period of the Y(t) for generating the $V_Y$ may be different than, but at least partly overlap, the time period of the Y(t) for generating the $S_{XY}$. In an example, the morphological variability metric $V_Y$ for a detected heart beat "k", denoted by $V_Y(k)$, may be computed using a morphological dissimilarity between the beat "k" and its neighboring beat, such as a heart beat immediately before or after the heart beat k. In an example, the morphological variability metric $V_Y(k)$ may be computed using a correlation between the morphological features {$Y_k$(i)} of beat "k" and the morphological features {$Y_{k-1}$(i)} or beat "k-1" (the beat immediately before beat "k"). In an example, the $V_Y(k)$ may be computed using an accumulated difference between {$Y_k$(i)} and {$Y_{k-1}$(i)}, as shown in Equation (4) below. In another example, the $V_Y(k)$ may be computed using an accumulated difference between {$Y_k$(i)} and {$Y_{k-1}$(i)} each weighted by respective weight factors, such as peak amplitudes $R_k$ and $R_{k-1}$ of the heart beats "k" and "k-1", respectively, as given in Equation (5) below. Equation (4) is similar to Equation (1) for determining the morphological similarity metric between {Y(i)} and {X(i)}. Equation (5) is similar to Equation (2) for determining the morphological similarity metric between {Y(i)} and {X(i)}. In yet another example, the morphological variability metric $V_Y$ (k) may be normalized by the weighted accumulated feature amplitudes of the detected heart beat "k", as shown in Equation (6) below.

$$V_Y(k) = \sum_{i=1}^{M} |Y_k(i) - Y_{k-1}(i)| \quad (4)$$

$$V_Y(k) = \sum_{i=1}^{M} |R_k \cdot Y_k(i) - R_{k-1} \cdot Y_{k-1}(i)| \quad (5)$$

$$V_Y(k) = \sum_{i=1}^{N} |R_k \cdot Y_k(i) - R_{k-1} \cdot Y_{k-1}(i)| / \sum_{i=1}^{M} |R_Y \cdot Y_k(i)| \quad (6)$$

The normalized morphological variability metric $V_Y$, according to Equation (6), is a bounded value between 0 and 1, which represents the degree of dissimilarity between the heart beats "k" and "k-1". A larger value (close to "1") indicates a higher degree of morphological variability between {$Y_k$(i)} and {$Y_{k-1}$(i)}. A smaller value (closer to "0") indicates a lower degree of morphological variability between the heart beats "k" and "k-1".

The atrial tachyarrhythmia detector 238 may detect an atrial tachyarrhythmia episode (e.g., an AF episode) using the morphological similarity metric and the morphological variability metric respectively produced by the morphology similarity calculator 234 and the morphological variability calculator 236. To detect an atrial tachyarrhythmia rhythm, the atrial tachyarrhythmia detector 238 may determine a first prevalence measure of the heart beats that are morphologically similar to the SR template, and a second prevalence measure of the heart beats that are morphologically distinct from the neighboring heart beat (e.g., a heart beat immediately before, or immediately after, the heart beat being analyzed). The first and second prevalence measures may each be determined over a specified time duration, or over a specified number of heart beats in the received physiologic signal. In an example, the first prevalence measure includes a count of heart beats, or a relative number of heart beats (e.g., a fraction or a percentage) in the received physiologic signal, that have corresponding morphology similarity metric $S_{XY}$ (such as computed according to Equation (3)) exceeding a morphology similarity threshold or falling into a specific range. The second prevalence measure includes a count of heart beats, in the received physiologic signal, each having a corresponding morphology variability metric $V_Y$ (such as computed according to Equation (6)) exceeding a morphology variability threshold or falling into a specific range. The atrial tachyarrhythmia detector 238 may detect an atrial tachyarrhythmia episode using one or more of the first and second prevalence measures. In an example, the atrial tachyarrhythmia detector 238 may detect an AF episode if a substantial amount or percentage of heart beats (e.g., exceeding a threshold) are determined to be morphologically similar to the SR template, or only a small amount or percentage of heart beats (e.g., falling below a threshold) are morphologically distinct from its neighboring heart beats. Examples of atrial tachyarrhythmia detection using the morphological similarity metric and the morphological variability metric are discussed below, such as with reference to FIG. 4.

The user interface 240 may include an input unit and an output unit. In an example, at least a portion of the user interface 240 may be implemented in the external system 125. The input unit may receive user input for programming the sensing circuit 210 and the arrhythmia detector circuit 230, such as parameters for detecting heart beat from a physiologic signal, parameters for extracting features, parameters (e.g., threshold values) for determining heart beats that are morphological similar to the SR template and for determining heart beats that are morphological distinct from its neighboring beats, or parameters (e.g., threshold values) for detecting an atrial tachyarrhythmia episode. The input unit may receive SR template (e.g., template features $\{X(i)\}$), or parameters for generating or updating the SR template. The input unit may include a keyboard, on-screen keyboard, mouse, trackball, touchpad, touch-screen, or other pointing or navigating devices.

The output unit may include a display for displaying the physiologic signal, extracted signal features, the SR template, the morphologic similarity metric and the morphologic variability metric, the detection decision of the atrial tachyarrhythmia episode, among other intermediate measurements or computations. The output unit may also present to a user, such as via a display unit, the therapy titration protocol or a recommended therapy, including a change of parameters in the therapy provided by an implanted device, the prescription to get a device implanted, the initiation or change in therapy, or other treatment options of a patient. The output unit may include a printer for printing hard copies of signals, computation results, or detected atrial tachyarrhythmia episode. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected atrial tachyarrhythmia episode.

The therapy circuit 250 may be configured to deliver a therapy to the patient, such as in response to the detected atrial tachyarrhythmia episode. The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 250 may modify an existing therapy, such as adjust a stimulation parameter or drug dosage.

Figure 3A:
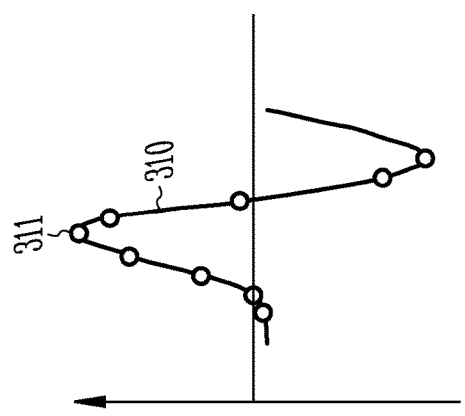
FIGS. 3A-3C are graphs illustrating examples of a reference signal morphology and comparison of a heart beat morphology to the reference signal morphology.
Figure 3B:
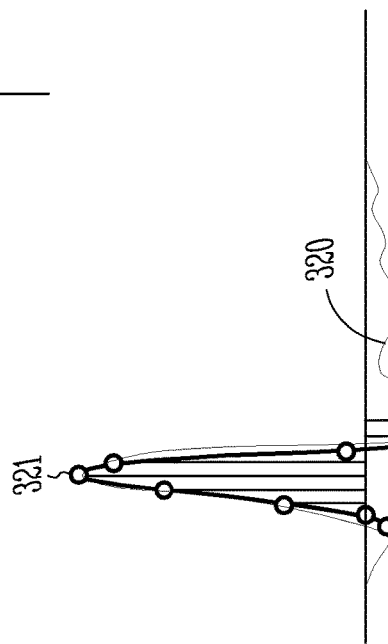
Figure 3C:
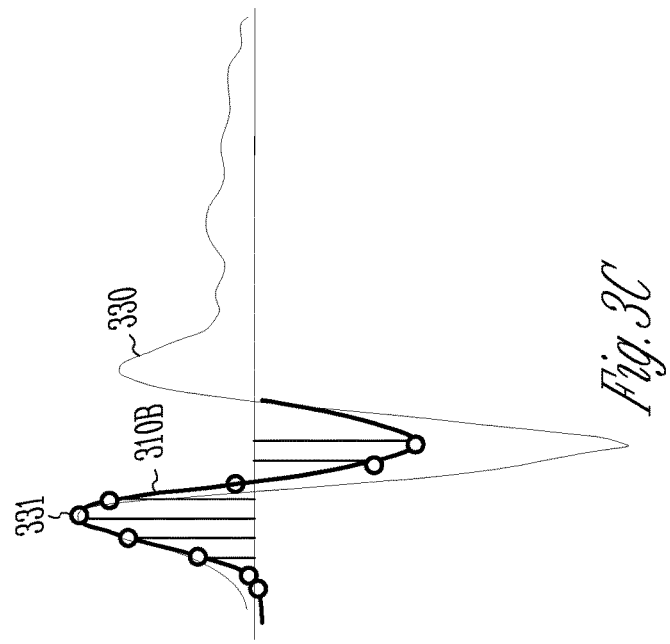

FIGS. 3A-3C are graphs illustrating examples of a reference signal morphology and comparison of a heart beat morphology to the reference signal morphology. Specifically, FIG. 3A illustrate an exemplary reference signal morphology 310 representing a portion of a heart beat taken from an ECG or intracardiac EGM during a cardiac cycle. The reference signal morphology 310 may comprise a specific number of morphological features extracted from the portion of the heart beat of the reference signal. By way of non-limiting example and as illustrated in FIG. 3A, the morphological features may include a subset of data samples, including a signal peak 311 and four data samples before and four data samples after the signal peak 311.

In an example, the reference signal morphology 310 represents a portion of a conducted sinus beat, or an ensemble average of multiple conducted sinus beats recorded during a sinus rhythm. The signal features on the signal morphology 310 represent an SR template $\{X(i)\}$, such as generated by the template circuit 220. In another example, the reference signal morphology 310 may be a portion of a heart beat in a physiologic signal not recorded during a sinus rhythm, such as the detected heart beat "k−1" as discussed above. The signal features on the signal morphology 310 represent signal features $\{Y_{k-1}(i)\}$ of the beat "k−1", such as generated by the feature extractor circuit 232.

FIGS. 3B-3C illustrate examples of morphological comparison between the reference signal morphology 310 and a portion of a detected heart beat, such as heart beat "k" detected from the sensed physiologic signal using the heart beat detector 212. The detected heart beat "k" may be aligned in time to the reference signal morphology 310 with respect to their respective fiducial points, such as the peak 311 of the reference signal morphology 310, and the peak of the heart beat "k". The morphological features of the reference signal morphology 310 may be scaled using a weight factor such as the value of the peak 311. Similarly, the heart beat "k" may be scaled using a weight factor such as its peak value. FIG. 3B illustrates one example of the heart beat "k" 320 having a peak 321, that is scaled, and peak-aligned with the scaled reference signal morphology 310A (a scaled version of the reference signal morphology 310). FIG. 3C illustrates another example of the heart beat "k" 330 having a peak 331, that is scaled and peak-aligned with the scaled reference signal morphology 310B (a scaled version of the reference signal morphology 310). Morphological features of heart beat "k", $\{Y_k(i)\}$, may be extracted respectively from the aligned and scaled waveform of the heart beat "k" 320 or 330, such as according to the same approach of feature extraction from the reference signal morphology 310. In an example, the morphological features of the heart beat "k" 320 or 330 are taken at same relative time offsets with respect to its peak 321 as those time offsets between the features on the reference signal morphology 310 with respect to its peak 311.

In the case that the reference signal morphology 310 represents a SR template $\{X(i)\}$, a morphologic similarity metric may be computed using the SR template $\{X(i)\}$ and the morphological features $\{Y_k(i)\}$ of heart beat "k", such as using the morphology similarity calculator 234. In the illustrated example, the heart beat "k" 320 in FIG. 3B is morphologically similar to the scaled reference signal morphology 310A. The heart beat "k" 320 is determined to match the SR template 310 if the morphologic similarity metric, such as computed using Equation (3), exceeds a similarity threshold. The heart beat "k" 330 in FIG. 3C is morphologically dissimilar to the scaled reference signal morphology 310B. The heart beat "k" 330 is determined to mismatch the SR template 310 if the morphologic similarity metric, such as computed using Equation (3), falls below the similarity threshold.

In the case that the reference signal morphology 310 represents morphological features $\{Y_{k-1}(i)\}$ of a heart beat such as beat "k−1" in the received physiologic signal, a morphologic variability metric may be computed between the morphological features $\{Y_k(i)\}$ and the morphological features $\{Y_{k-1}(i)\}$ of the heart beat "k−1", such as using the morphology variability calculator 236. In the illustrated example, the heart beat "k" 320 in FIG. 3B is morphologically similar to the scaled signal morphology of heart beat "k−1" 310B. The heart beat "k" 320 is determined to be morphologically consistent with the neighboring heart beat "k−1" 310 if the morphologic variability metric, such as computed using Equation (6), falls below a threshold. The heart beat "k" 330 in FIG. 3C is morphologically distinct from the scaled signal morphology of heart beat "k−1" 310B. The heart beat "k" 330 is determined to be morphologically variable over the neighboring heart beat "k−1" 310 if the morphologic variability metric, such as computed using Equation (6), exceeds a threshold.

FIG. 4 is a graph illustrating an exemplary scheme 400 of detecting atrial tachyarrhythmia, such as an AF episode, using the morphological similarity metric and the morphological variability metric calculated for the detected heart beats in a sensed physiologic signal. The illustrated scheme 400 may be implemented in and executed by the atrial tachyarrhythmia detector 238. The atrial tachyarrhythmia detection given in this example is based on the prevalence of heart beats that are morphologically similar to the SR template, and the prevalence of heart beats that are morphologically variable to each other (e.g., beat-to-beat morphologic variability between neighboring heart beats). In FIG. 4, the x-axis represents a percentage of heart beats that are morphologically similar to the SR template, or to match the SR template. During atrial tachyarrhythmia such as AF, at least in some patients, the atrial activations may be intermittently conducted to the ventricle via the physiologic atrioventricular conduction system, such that the heart beats have morphologies similar to the SR template. As such, a larger percentage value in the x-axis may indicate a higher likelihood of presence of AF. As illustrated in FIG. 4, an atrial tachyarrhythmia episode is detected when the percentage of heart beats that match the SR template exceeds a first threshold $TH_1$. The first threshold $TH_1$ may be adjustable by a user, such as via the user interface 240. In an example, the threshold value $TH_1$ is approximately 50-80%.

The y-axis represents a percentage of heart beats that are morphologically variable, such as distinct from its neighboring heart beat according to a morphology comparison criterion. Conducted atrial activations through the atrioventricular conduction pathways generally have consistent morphologies. For aberrant ventricular conductions that occur during AF such as due to refractoriness in the right or left bundle branch, even though they may present with wide QRS morphologies dissimilar to the SR template, may nevertheless have consistent, or less variable, beat-to-beat morphologies. Therefore, AF with aberrant ventricular conductions, which would otherwise be missed or inappropriately detected as a ventricular tachyarrhythmia by a SR template-based method, may be correctly detected using the morphological variability metric. A smaller percentage value in the y-axis indicates less morphological variability between heart beats, and thus a higher likelihood of presence of AF. As illustrated in FIG. 4, an atrial tachyarrhythmia episode is detected when the percentage of morphologically variable heart beats (e.g., heart beats having inconsistent morphology with the neighboring beats) falls below a second threshold $TH_2$. The second threshold $TH_2$ may be adjustable by a user, such as via the user interface 240. In an example, the threshold value $TH_2$ is approximately 50-80%.

The scheme 400 and the atrial tachyarrhythmia detector 238 as illustrated in FIG. 2 both detect atrial tachyarrhythmia using the morphological similarity metric and the morphological variability metric. In an example, the atrial tachyarrhythmia detection based on morphological similarity metric and the morphological variability metric discussed herein may be used to boost performance of an arrhythmia detector (e.g., one based on morphological similarity only, or based on non-morphological features). For example, some atrial tachyarrhythmia episodes that would otherwise be missed or inappropriately detected by the morphological similarity-based detector can be rescued or recovered using morphological variability metric.

Figure 5:
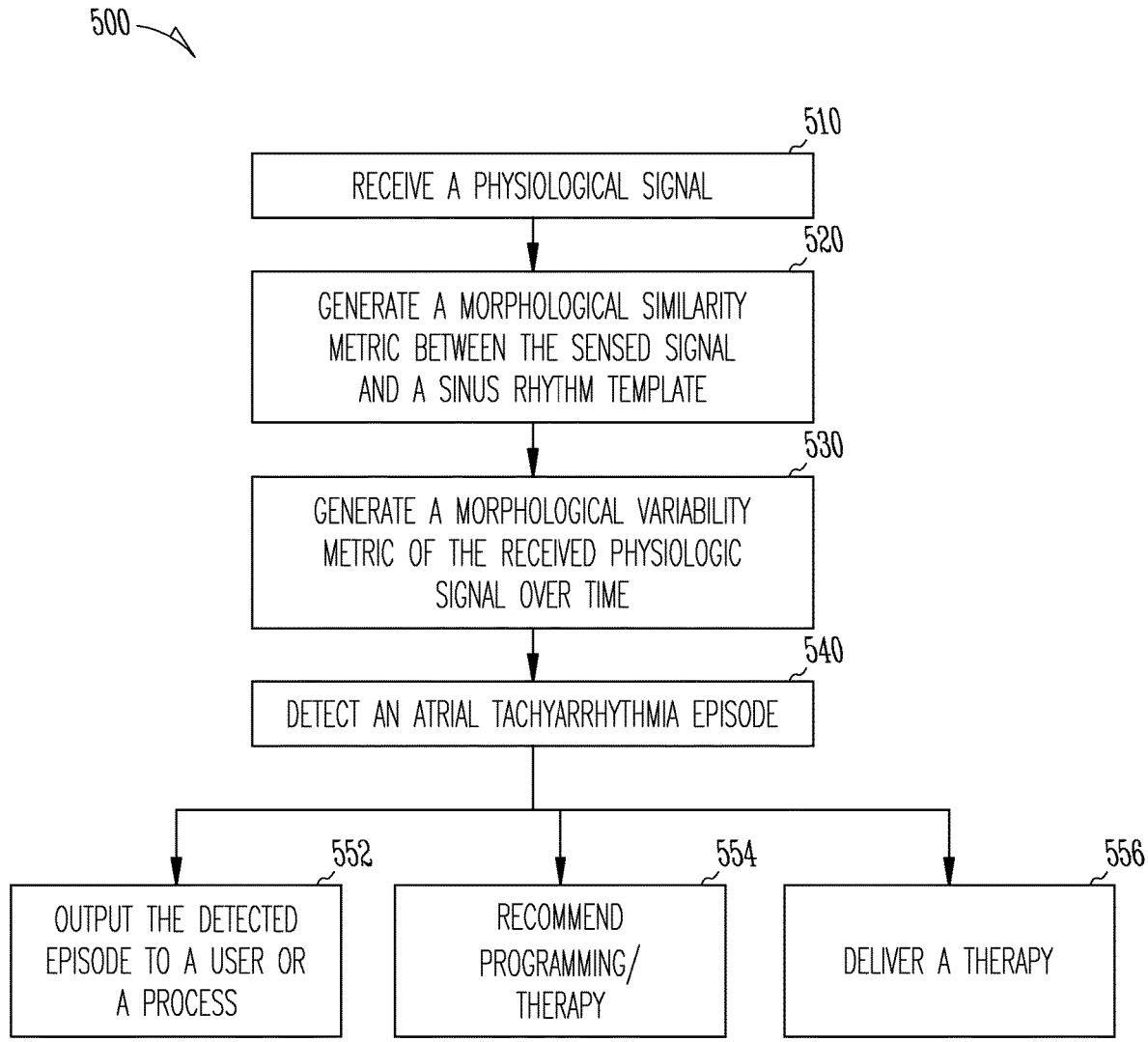
FIG. 5 illustrates generally an example of a method for detecting an atrial tachyarrhythmia from a patient.

FIG. 5 illustrates generally an example of a method 500 for detecting an atrial tachyarrhythmia from a patient. Examples of atrial tachyarrhythmia may include atrial fibrillation (AF), atrial flutter (AFL), atrial tachycardia, or paroxysmal supraventricular tachycardia (PSVT), among others. The method 500 may be implemented and executed in an ambulatory medical device such as an implantable or wearable medical device, or in a remote patient management system. In an example, the method 500 may be implemented in and executed by the cardiac arrhythmia detection circuit 160 in the AMD 110, the external system 130, or the arrhythmia detection system 200.

The method 500 commences at 510, where a physiologic signal may be sensed from a patient. The physiologic signal may include a cardiac electrical signal such as an ECG or an intracardiac EGM. The physiologic signals may additionally or alternatively include signals indicative of cardiac mechanical activity, including thoracic or cardiac impedance signal, arterial pressure signal, pulmonary artery pressure signal, left atrial pressure signal, RV pressure signal, LV coronary pressure signal, heart sounds or endocardial acceleration signal, physiologic response to activity, apnea hypopnea index, one or more respiration signals such as a respiration rate signal or a tidal volume signal, among others. The sensed physiologic signal may be pre-processed, including one or more of signal amplification, digitization, filtering, or other signal conditioning operations. Heart beats may be detected from the received physiologic signal, such as using the heart beat detector 212.

At 520, a morphological similarity metric may be generated, such as using the morphology similarity calculator 234 as illustrated in FIG. 2. The morphological similarity metric may be computed between the received physiologic signal and a SR template representing a morphology of conducted sinus beats during normal SR. The SR template may include SR morphology features extracted from an ensemble average of a plurality of conducted SR heart beats. In an example, the SR morphology features may include amplitude of data samples $\{X(i)\}$ of a cardiac electrical signal $X(t)$ within a cardiac cycle or a portion of the cardiac cycle such as the QRS complex. Morphological features may be extracted from the heart beat detected from the received physiologic signal, such as using the feature extractor circuit 232. The morphological features may include amplitude of data samples $\{Y(i)\}$ within a cardiac cycle or a portion of the cardiac cycle such as the QRS complex. In an example, the detected heart beat may be aligned to the conducted sinus beat of the SR template before extracting the morphological features $\{Y(i)\}$ from the detected heart beat. The alignment may be with respect to a fiducial point on the detected heart beat and a fiducial point on the conducted sinus beat corresponding to the SR template, such as a peak of the detected heart beat of the received physiologic signal, and a peak of the conducted sinus beat corresponding to the SR template.

A morphological similarity metric may be computed between the morphological features $\{Y(i)\}$ of a detected heart beat "k" of the sensed physiological signal, and SR morphology features {X(i)} of the SR template. The morphological similarity metric may be computed using a correlation, or an accumulated difference between the signal features and SR morphology features, such as according to one of the Equations (1)-(3) as discussed above.

At 530, a morphological variability metric may be generated, such as using the morphology variability calculator 236. The morphological variability metric represents changes in morphology of the received physiologic signal over time. In an example, the morphological variability metric may be computed using beat-to-beat variability of the heart beats detected from the sensed physiologic signal, such as between two consecutive detected heart beats "k" and "k−1". The two consecutive detected heart beats have respective set of signal features, $\{Y_k(i)\}$ and $\{Y_{k-1}(i)\}$, which may contain the same number of features. A morphological variability metric may be computed between the morphological features $\{Y_k(i)\}$ of a detected heart beat "k" and the morphological features $\{Y_{k-1}(i)\}$ of a detected heart beat "k−1". The morphological variability metric may be computed using a correlation, or an accumulated difference, between the signal features $\{Y_k(i)\}$ and $\{Y_{k-1}(i)\}$, such as according to one of the Equations (4)-(6) as discussed above.

At 540, an atrial tachyarrhythmia episode may be detected using the morphological similarity metric and the morphological variability metric. A first prevalence measure of the heart beats that are morphologically similar to the SR template, and a second prevalence measure of the heart beats that are morphologically distinct from the neighboring heart beat (e.g., a heart beat immediately before, or immediately after, the heart beat being analyzed), may be determined, such as using the atrial tachyarrhythmia detector 238. The first and second prevalence measures may each be determined over a specified time duration, or over a specified number of heart beats in the received physiologic signal. In an example, the first prevalence measure includes a count of heart beats, or a relative measure such as a fraction or percentage of heart beats, with the corresponding morphology similarity metric exceeding a morphology similarity threshold or falling into a specific range, and the second prevalence measure includes a count of heart beats with the corresponding morphology variability metric $V_Y$ exceeding a morphology variability threshold or falling into a specific range. In an example, an atrial fibrillation (AF) episode is deemed detected if the first prevalence measure exceeds a first threshold $TH_1$, or the second prevalence measure falls below a second threshold $TH_2$. The threshold values $TH_1$ and $TH_2$ may be independently programmed or otherwise selected by a user (e.g., a clinician). In an example, the $TH_1$ and/or $TH_2$ take values between approximately 50-80%.

The detected atrial tachyarrhythmia event may be used in one or more of the processes 552, 554, or 556. At 552, the detected atrial tachyarrhythmia episode may be output to a user or a process, such as via the user interface 240 illustrated in FIG. 2. In an example, information may be displayed on a display, including the physiologic signal, extracted signal features, the SR template, the morphologic similarity metric and the morphologic variability metric, the detection decision of the atrial tachyarrhythmia episode, among others. Additionally or alternatively, a hard copy of the detection information may be generated.

At 554, a recommendation may be generated and provided to the user. The recommendation may include one or more of further diagnostic tests to be performed, anti-arrhythmic therapy to treat the detected arrhythmia or to alleviate the arrhythmic complications. The recommendation may include adjustment of one or more arrhythmia detection parameters, such as the threshold for determining morphological similarity to the SR template, the threshold for determining morphological variability between detected heart beats from the received physiologic signal, time duration or number of heart beats to be analyzed for computing the first and second prevalence measures, and prevalence thresholds $TH_1$ and $TH_2$, among others. In some examples, the system user may review and adjudicate the detected atrial tachyarrhythmia episode, and reprogram one or more detection parameters.

The method 500 may include the optional step 556 of delivering a therapy to the patient in response to the detection of the cardiac arrhythmia, such as via the optional therapy circuit 250 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia, such as modify patient follow-up schedule, or adjust a stimulation parameter or drug dosage.

Figure 6:
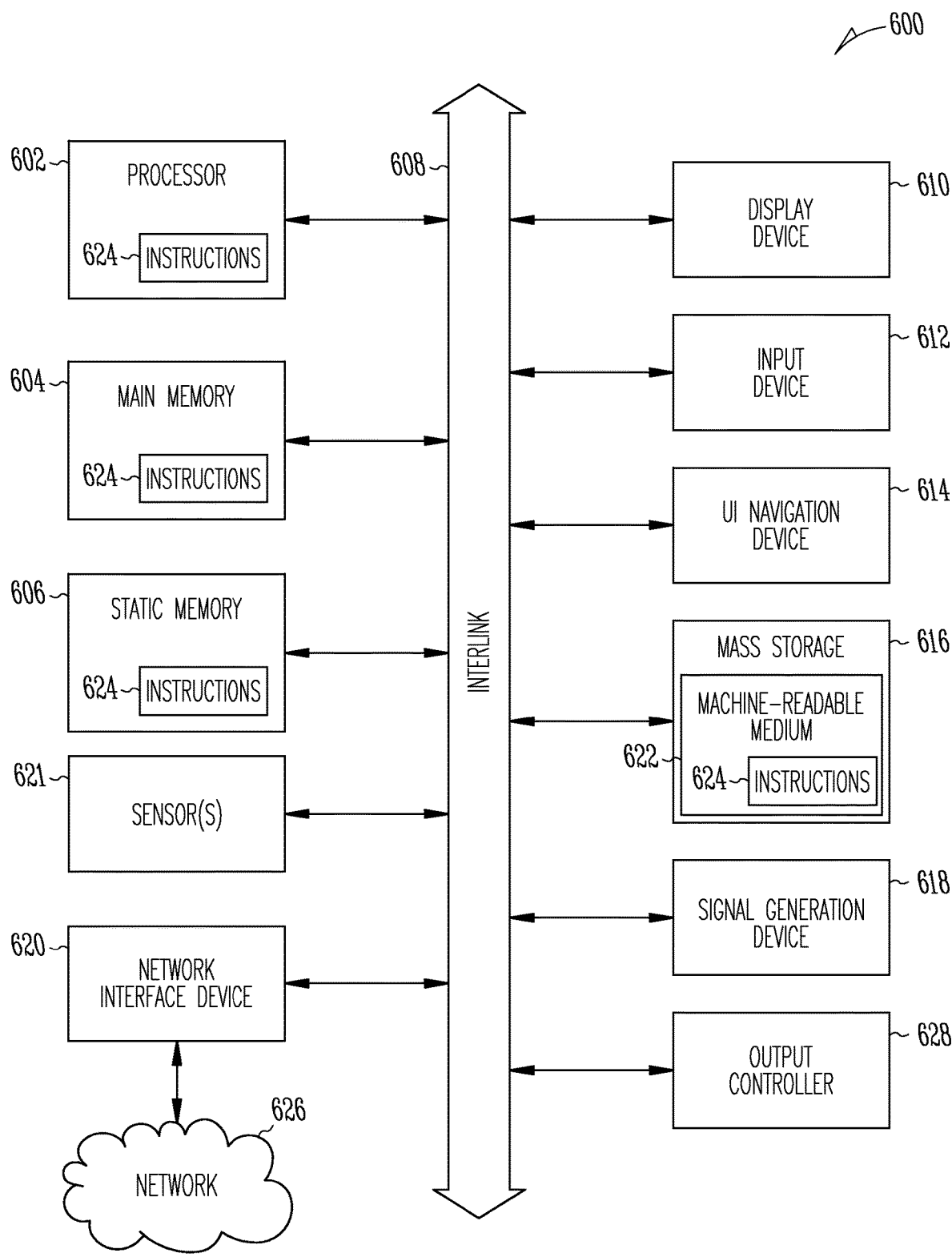
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the IMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for detecting atrial tachyarrhythmia, comprising:
   an arrhythmia detector circuit configured to:
      receive physiologic information of a patient;
      generate a morphological similarity metric between the received physiologic information and a sinus rhythm (SR) template, the SR template representing a morphology of conducted sinus beats during normal SR;
      generate a morphological variability metric indicative of a variability in morphology between heart beats in the received physiologic information;

determine a first count of heart beats with corresponding morphology similarity metric exceeding a morphology similarity threshold, and a second count of heart beats with corresponding morphological variability metric exceeding a morphological variability threshold; and detect an atrial tachyarrhythmia episode in response to the first count of heart beats exceeding a first count threshold, or the second count of heart beats being below a second count threshold.

2. The system of claim 1, wherein the SR template includes SR morphology features representing amplitudes of data samples of the conducted sinus beat, and the arrhythmia detector circuit is configured to:

detect a heart beat from the received physiologic information;

generate signal features from the detected heart beat, the generated signal features including amplitudes of data samples of the detect heart beat; and compute the morphological similarity metric using the generated signal features of the detected heart beat and the SR morphology features.

3. The system of claim 2, wherein the arrhythmia detector circuit is configured to align the detected heart beat with the conducted sinus beat using a fiducial point of the detected heart beat and a fiducial point of the conducted sinus beat corresponding to the SR template.

4. The system of claim 2, wherein the arrhythmia detector circuit is configured to generate the morphological similarity metric using an accumulated difference between the generated signal features of the detected heart beat and the SR morphology features.

5. The system of claim 2, wherein the arrhythmia detector circuit is configured to generate the morphological similarity metric using an accumulated difference between (1) the generated signal features of the detected heart beat each weighted by a peak amplitude of the detected heart beat and (2) the SR morphology features each weighted by a peak amplitude of the conducted sinus beat.

6. The system of claim 1, comprising a template circuit configured to generate or update the SR template using a physiologic signal sensed during the SR.

7. The system of claim 6, wherein the template circuit is configured to generate or update the SR template including to compute an ensemble average of a plurality of conducted sinus beats during normal SR, and to generate or update the SR template using the computed ensemble average of the plurality of conducted sinus beats.

8. The system of claim 1, wherein the arrhythmia detector circuit is configured to:

detect first and second heart beats from the received physiologic information;

align the first heart beat with the second heart beat with respect to respective fiducial points of the first and second heart beats;

generate first and second signal features respectively from the aligned first and second heart beats; and compute the morphological variability metric indicative of a dissimilarity between the generated first and second signal features.

9. The system of claim 8, wherein the arrhythmia detector circuit is configured to compute the morphological variability metric using an accumulated difference between the generated first and second signal features.

10. The system of claim 8, wherein the arrhythmia detector circuit is configured to compute the morphological variability metric using an accumulated difference between (1) the generated first signal features each weighted by a peak amplitude of the detected first heart beat and (2) the generated second signal features each weighted by a peak amplitude of the detected second heart beat.

11. The system of claim 1, comprising a therapy circuit configured to initiate or adjust a therapy in response to the detected atrial tachyarrhythmia episode.

12. A system for detecting atrial tachyarrhythmia, comprising:

an arrhythmia detector circuit configured to:

receive physiologic information of a patient;

generate a morphological similarity metric between the received physiologic information and a sinus rhythm (SR) template, the SR template representing a morphology of conducted sinus beats during normal SR;

determine a count of heart beats with corresponding morphology similarity metric exceeding a morphology similarity threshold; and detect an atrial tachyarrhythmia episode in response to the count of heart beats exceeding a count threshold.

13. The system of claim 12, wherein the SR template includes SR morphology features representing amplitudes of data samples of the conducted sinus beat, and the arrhythmia detector circuit is configured to:

detect a heart beat from the received physiologic information;

generate signal features from the detected heart beat, the generated signal features including amplitudes of data samples of the detect heart beat; and compute the morphological similarity metric using the generated signal features of the detected heart beat and the SR morphology features.

14. The system of claim 13, wherein the arrhythmia detector circuit is configured to generate the morphological similarity metric using an accumulated difference between the generated signal features of the detected heart beat and the SR morphology features.

15. The system of claim 13, wherein the arrhythmia detector circuit is configured to generate the morphological similarity metric using an accumulated difference between (1) the generated signal features of the detected heart beat each weighted by a peak amplitude of the detected heart beat and (2) the SR morphology features each weighted by a peak amplitude of the conducted sinus beat.

16. The system of claim 12, comprising a template circuit configured to compute an ensemble average of a plurality of conducted sinus beats during normal SR, and to generate or update the SR template using the computed ensemble average of the plurality of conducted sinus beats.

17. A system for detecting atrial tachyarrhythmia, comprising:

an arrhythmia detector circuit configured to:

receive physiologic information of a patient;

generate a morphological variability metric indicative of a variability in morphology between heart beats in the received physiologic information;

determine a count of heart beats with corresponding morphological variability metric exceeding a morphological variability threshold; and detect an atrial tachyarrhythmia episode in response to the count of heart beats being below a count threshold.

18. The system of claim 17, wherein the arrhythmia detector circuit is configured to:

detect first and second heart beats from the received physiologic information;

align the first heart beat with the second heart beat with respect to respective fiducial points of the first and second heart beats;
generate first and second signal features respectively from the aligned first and second heart beats; and
compute the morphological variability metric indicative of a dissimilarity between the generated first and second signal features.

19. The system of claim 18, wherein the arrhythmia detector circuit is configured to compute the morphological variability metric using an accumulated difference between the generated first and second signal features.

20. The system of claim 18, wherein the arrhythmia detector circuit is configured to compute the morphological variability metric using an accumulated difference between (1) the generated first signal features each weighted by a peak amplitude of the detected first heart beat and (2) the generated second signal features each weighted by a peak amplitude of the detected second heart beat.

* * * * *